United States Patent [19]

Crispin

[11] Patent Number: 4,771,768
[45] Date of Patent: Sep. 20, 1988

[54] CONTROLLED MOTION ANKLE FRACTURE WALKER

[75] Inventor: George E. Crispin, La Canada, Calif.
[73] Assignee: United States Manufacturing Company, Pasadena, Calif.
[21] Appl. No.: 942,352
[22] Filed: Dec. 16, 1986
[51] Int. Cl.$^4$ .............................................. A61F 5/04
[52] U.S. Cl. ..................................... 128/88; 128/83.5; 128/80 H; 128/166
[58] Field of Search ............... 128/83, 83.5, 88, 80 H, 128/80 R, 80 F, 87 R, 166, 252

[56] References Cited

U.S. PATENT DOCUMENTS

| | | | |
|---|---|---|---|
| 2,141,099 | 12/1938 | Walters | 128/83.5 |
| 4,057,056 | 11/1977 | Payton | 128/83.5 |
| 4,489,718 | 12/1984 | Martin | 128/88 |
| 4,517,968 | 5/1985 | Greene et al. | 128/166 X |
| 4,621,648 | 11/1986 | Ivany | 128/166 X |

Primary Examiner—Robert A. Hafer
Assistant Examiner—Kevin G. Rooney
Attorney, Agent, or Firm—Christie, Parker & Hale

[57] ABSTRACT

A controlled motion ankle fracture walker includes a foot supporting rocker to which the foot of a patient is releasably secured, and a leg support wrapped around the patient's lower leg above the ankle joint. The foot support includes a rigid shell with a curved bottom forming a rocker for rolling contact with the ground to provide a rocking heel to toe motion of the patient's foot during weight bearing. Rigid lateral and medial uprights are rigidly affixed alongside the leg support, and adjustable double action ankle joints pivotly interconnect the bottoms of the uprights with the rigid support arms on the lateral and medial sides of the foot supporting shell. The ankle joints permit adjustable range of motion of the uprights in dorsiflexion or plantar flexion. The walker allows the patient to apply weight to the ankle joint during a normal walking gait while the ankle joint can be flexed through a controlled degree of dorsiflexion, plantar flexion, or both, by the front to rear settings of the adjustable double action ankle joints.

8 Claims, 5 Drawing Sheets

CONTROLLED MOTION ANKLE FRACTURE WALKER

FIELD OF THE INVENTION

This invention relates to orthotic devices, and more particularly to an ankle fracture walker having controlled ankle motion for speeding the rehabilitation time required for ankle fractures, severe ankle sprains, and other injuries to the ankle joint or the foot.

BACKGROUND OF THE INVENTION

Over the past several years, a number of orthotic braces referred to as "walkers" have been developed for replacing use of plaster walking casts which have previously been used in the rehabilitation of ankle fractures. Normally, an ankle fracture is treated by holding the foot in a neutral position and immobilizing the ankle in a rigid cast from below the knee to the toes. After six to eight weeks a walking boot cast is applied and weight bearing is permitted. The walking boot cast also immobilizes the ankle joint.

The ankle fracture walkers have many advantages over the rigid walking boot cast. The ankle fracture walkers are easily removable from the lower leg, ankle and foot, and they can be easily placed back in a supporting position, often without the assistance of a medical professional.

These ankle fracture walkers generally include a foot supporting shoe, referred to as a "rocker", which includes a rigid shell that fits around and under the foot. A curved sole on the bottom of the shell permits a rocking heel-to-toe motion of the foot during use. The rocker usually attaches to the leg of the patient by rigid or semi-rigid uprights extending along the lateral and medial sides of the leg above the ankle joint. The uprights are commonly affixed to a semi-rigid or soft means of support that wraps around the lower leg and ankle joint. Fasteners carried on the upper portion of the walker are wrapped around the patient's leg to provide the necessary support, and similar fasteners firmly affix the rocker to the patient's foot. The bottoms of the uprights are rigidly affixed to the opposite sides of the rocker to immobilize the patient's ankle joint so as to hold the ankle joint at a fixed angle of about 90° (the angle defined by the lower leg and the ground) when the walker is in use. Some ankle fracture walkers may immobilize the patient's ankle joint in a slight angle from 90°, depending upon the injury.

The natural configuration of the rocker permits the patient to closely simulate a normal walking gait while wearing the walker, while the affected ankle joint is stabilized to limit motion in any direction. As a result, the patient's ankle is held at the fixed angle while weight can be applied to the affected area during walking. The walking motion is assisted by the rounded bottom configuration of the rocker.

Prior art walkers have primarily been used in the rehabilitation of stable ankle or foot fractures usually following surgery. They also have been used during rehabilitation of severe ankle sprains or strains or other ligament damage to the ankle. The prior art walkers have provided many advantages to the patient when compared with a rigid cast. For instance, they save time normally required to apply a plaster cast, and cast complications are avoided. The walker can be applied in an adjustable snug fit and can be easily removed. This provides convenient access to the afflicted joint. Since the patient can come out of the cast earlier and begin walking, healing is improved and the rehabilitation period is shortened as a result of weight-bearing while walking. Weight-bearing decreases atrophy, maintains proprieception, and reduces edema.

The present invention is directed to an ankle fracture walker that significantly improves the rehabilitation process for an ankle fracture in a manner that is not possible with the proir art walkers described above. The walker of this invention allows a controlled angular range of ankle motion during weight-bearing on the ankle joint while the ankle joint is supported by the walker and while the patient walks at a normal walking gait controlled by the walker. As a result, the ankle fracture walker greatly enlarges the methods of treatment of ankle fractures during the rehabilitation process. The ankle fracture walker can be adjusted throughout the rehabilitation process to allow maximum mobility of the ankle joint during weightbearing, depending upon the type of injury involved and the patient's progress in healing. Rehabilitation is functionally better for the patient and total rehabilitation time is reduced when compared with patients using the prior art fixed-angle walkers.

SUMMARY OF THE INVENTION

Briefly, the invention comprises a controlled ankle motion walker which includes a foot support with a curved bottom for rolling contact with the ground to provide a rocking motion fot the foot of a patient secured to the foot support. The foot support includes a rigid shell which extends along lateral and medial sides of the foot, below the ankle joint. A leg support is secured to the lower leg of the patient above the ankle joint. The leg support at least has rigid lateral and medial means of support extending along the lateral and medial sides, respectively, of the lower leg above the ankle joint. Adjustable double action ankle joints adjacent the lateral and medial sides of the ankle joint interconnect the lateral and medial support means on the leg support and the lateral and medial sides of the shell, respectively. The double action ankle joints provide a means for allowing the patient's ankle joint to flex, i.e., to move forward or backwards as opposed to twisting or moving from side to side (also referred to as inversion or eversion). Such flexion is controlled during weight-bearing when the walker is used during the patient's normal walking gait. The controlled angular flexion of the patient's ankle joint is provided by the double action ankle joints, adjustment of the angle through which the leg support can flex forward or backwards relative to the foot support. The double action ankle joint can be adjusted to set a fixed angular position between the leg support and the foot support to hold the patient's ankle joint in a fixed angular position during walking; or the double action ankle joint can be adjusted to set a range of motion, in either dorsiflexion or plantar flexion, or both. The patient wearing the walker can apply weight to the ankle joint during rehabilitation by walking with the assistance of the walker, while a controlled range of angular motion of the ankle joint also can be set by the physician to enhance mobilization of the affected tissues in combination with the weight-bearing. Thus, by promoting a progressive functional activity of the ankle joint during the rehabilitation process, the walker can promote osteogenesis, maintain muscle tone, reduce swelling, and shorten total rehabilitation time.

The controlled ankle motion walker of this invention provides substantial improvements over the prior art fixed-angle walkers. The prior art walker must first be removed before the ankle joint can undergo range of motion exercises. Moreover, progressive weight-bearing coupled with controlled angular motion of the ankle joint speeds rehabilitation as quickly as possible. The walker of this invention also adds certainty to the amount of angular motion allowed, because the amount and direction of angular travel can be precisely set by the physician depending upon the type of injury and the patient's rehabilitation progress. For instance, the walker can be set to allow the ankle to flex through a certain angle of dorsiflexion, or a certain angle of plantar flexion, or both, depending upon the type of injury. The walker thus allows progressive weightbearing, with support, pain-free by properly set angles of flexion, depending upon the injury, and this enables the patient to return to functional activity as quickly as possible.

These and other aspects of the invention will be more fully understood by referring to the following detailed description and the accompanying drawings.

DETAILED DESCRIPTION

Figure 1:
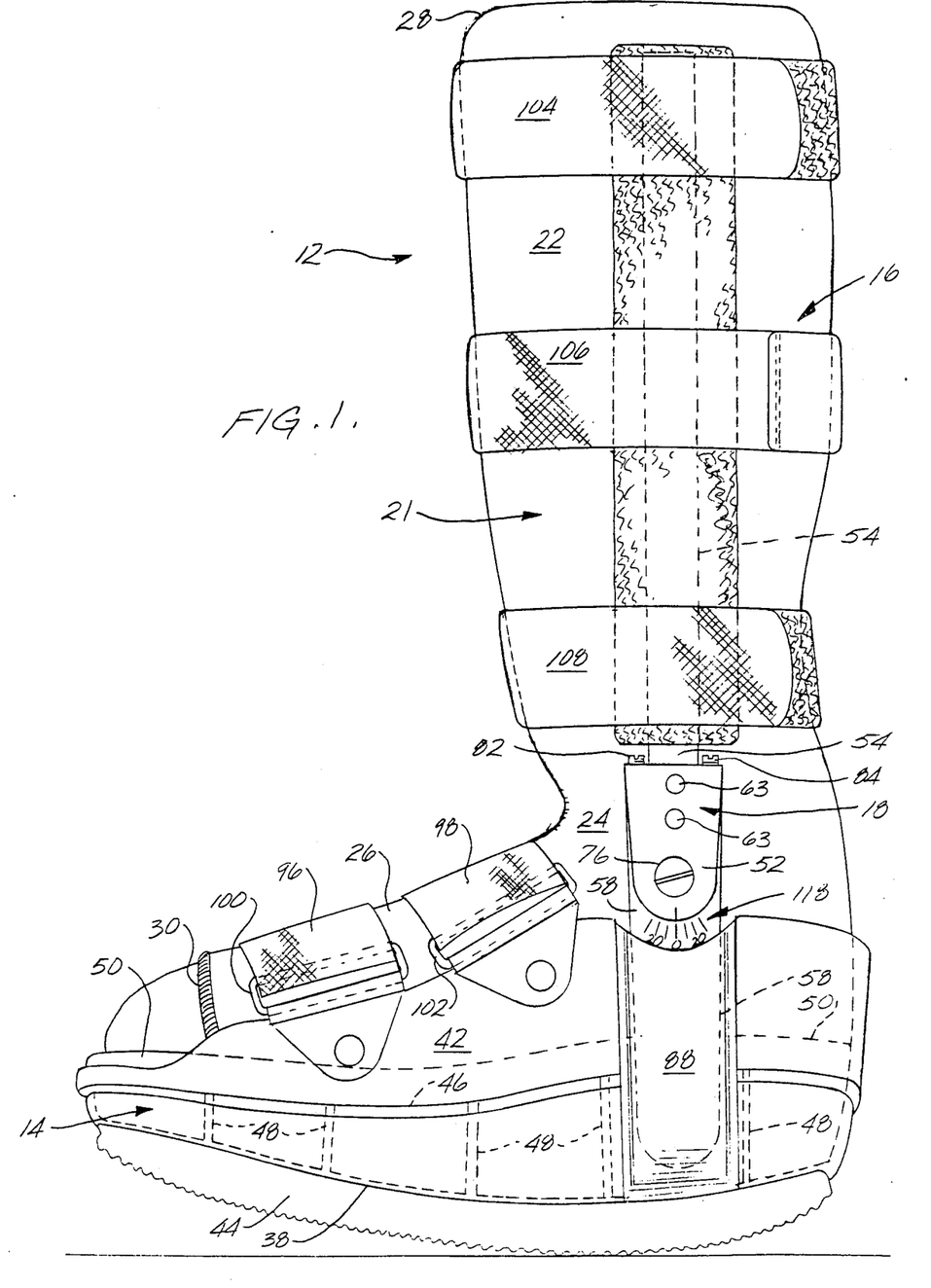
FIG. 1 is a side elevation view showing a controlled ankle motion walker according to principles of this invention.
Figures 2, 3:
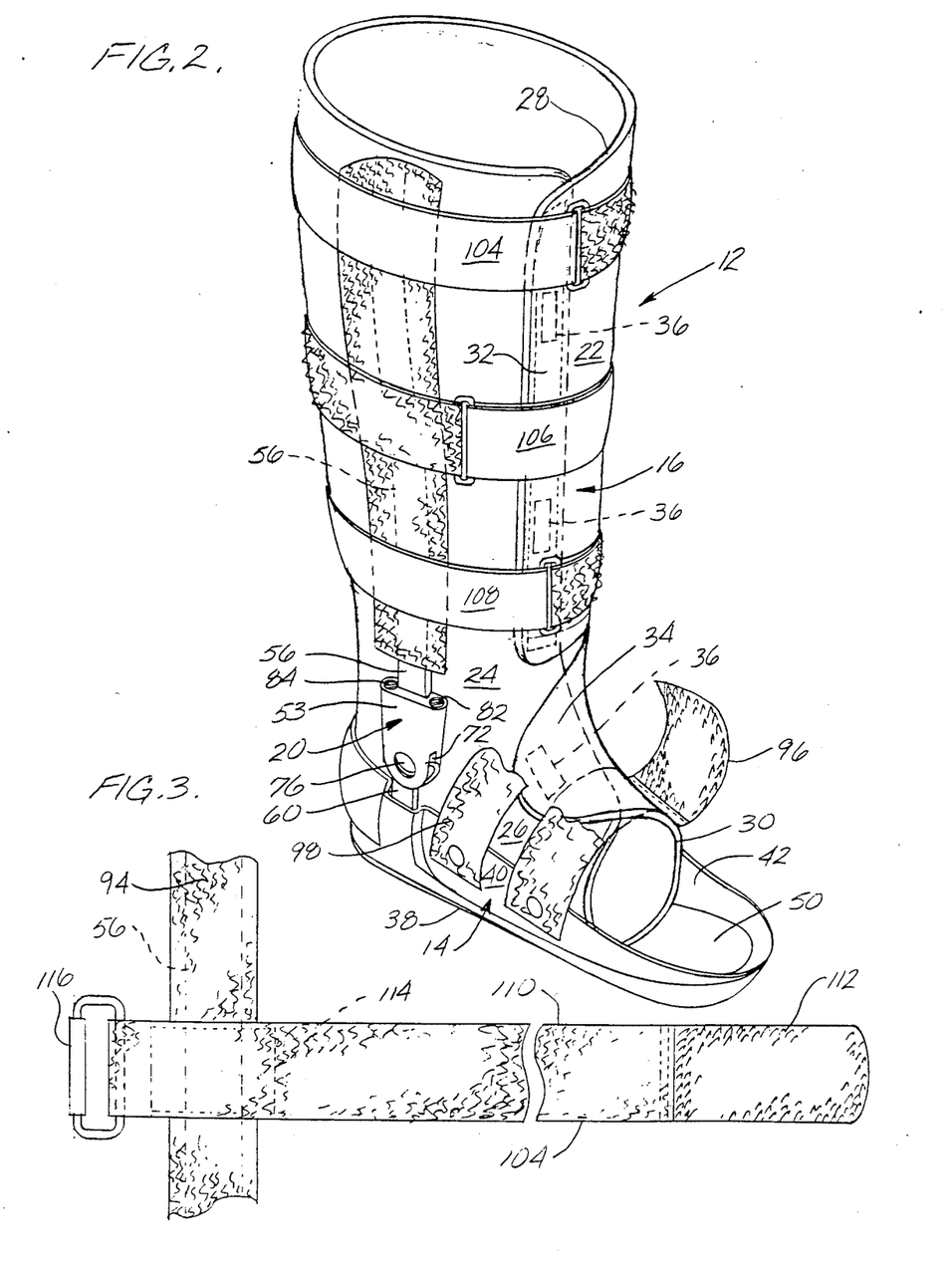
FIG. 2 is a perspective view, partly fragmentary and partly broken away, illustrating the walker of this invention.
FIG. 3 is a fragmentary elevation view illustrating a means of providing compression support on the lower leg for the walker in use.

Referring to FIGS. 1 and 2, a controlled motion ankle fracture walker 12 according to principles of this invention includes a rocker-type foot-supporting shoe 14 for attachment to the foot of a patient, a lower leg support 18 for attachment to the lower leg of the patient above the ankle joint, and medial and lateral double action ankle joints 18 and 20, respectively, overlying the medial and lateral ankle joints of the patient and interconnecting the medial and lateral sides of the lower leg support to corresponding sides of the shoe.

The walker also includes a soft, flexible sleeve 21 in the form of resilient (compressible in thickness) padding which wraps around the lower leg, the ankle region and the foot of the patient. This sleeve is generally L-shaped and extends around the entire circumference of the lower leg, the ankle region and the foot of the patient continuously from below the knee joint past the ankle joint to near the end of the foot. The sleeve thus includes an upper section 22 which wraps around the circumference of the lower leg and extends from below the knee joint to approximately the instep region of the foot above the ankle joint, an L-shaped ankle section 24 which wraps around the ankle region, and a foot section 26 which wraps around most of the length of the foot. One preferred embodiment of the sleeve is in the form of a laminated material comprising an outer layer of brushed Velcro-sensitive nylon, a middle layer of two-pound density polyester foam, and an inner layer of acetate Tricot. The soft, flexible sleeve has a continuous front opening extending the full length of the sleeve so that the front portion of the sleeve can open apart continuously from an upper opening 28 at the top of the sleeve, along the upper section 22, along the ankle region 24 and the foot section 28 of the sleeve, to a lower opening 30 near the end of the foot section 26. One side of the upper portion 22 of the sleeve is formed as a flexible upper flap to overlap the opposite side of the sleeve along the front opening to form a long straight closure 32 extending along the front upper portion 22 of the sleeve. One side of the foot section 26 of the sleeve is similarly formed as a flexible lower flap 34 to form a closure extending along the top of the foot section of the sleeve. Several vertically spaced apart Velcro hook type fasteners 38 are secured to the inside of the flaps and are frictionally fastened to the Velcro-sensitive outer face of the soft flexible sleeve for holding the sleeve in a comfortable but snug fit around the lower leg, the ankle region and the foot of the patient.

The rocker-type foot supporting shoe 14 includes a rigid open top shell which is generally U-shaped in cross section to form a long curved bottom surface 38 with lateral and medial side walls 40 and 42 extending above the bottom surface of the shell. A rugged slip-resistant sole 44 preferably made from a durable, slip-resistant and somewhat resilient material is secured to the curved bottom surface of the shell. The preferred material is a composite rubber-fabric material commonly used for conveyor belts. The bottom of the sole 44 matches the curved contour of the shell. The curved bottom surface of the rocker has a roll point located on a continuous radius extending from the toe to the heel region of the rocker to eliminate flat spots for a smooth patient gait to provide optimum walking assistance. The inside of the rocker has a rigid footsupporting interior surface 46 spaced above the curved bottom surface 38 of the rocker. The interior surface 46 is of contoured curvature and is shown best in FIG. 1. This surface has its highest elevation near the heel portion of the rocker and curves downwardly toward the middle section of the rocker and then curves upwardly toward the toe section of the rocker. This interior foot-supporting supporting surface can be a continuous surface; but preferably, inasmuch as the rocker is made from a high impact rigid plastic material, the rocker is molded so that the top of the interior surface 46 is formed by the top edges of spacedapart and parallel longitudinal ribs integral with perpendicular spaced-apart parallel lateral ribs 48 molded into the inside bottom portion of the rocker. The view of FIG. 1 illustrates the lateral ribs 48. The tops of the longitudinal ribs are curved longitudinally to form the contoured curvature of the top surface 46 illustrated in FIG. 1. A foot pad 50 is normally placed on top of the rigid footsupporting surface 46 of the rocker, below the foot region 26 of the soft flexible sleeve.

The double action ankle joints 18 and 20 are aligned on the medial and lateral sides of the ankle joint on a common axis of rotation through the ankle joint of the patient. Although forward and backwards rotation (flexion) of the ankle joint is actually about a polycentric axis, such flexion is approximately about a common transverse axis and the double action ankle joints are aligned to pivot about such a transverse axis. The medial and lateral double action ankle joints include separate medial and lateral brackets 52 and 53, respectively, rigidly affixed to lower portions of corresponding medial and lateral uprights 54 and 56. The uprights are preferably made from a rigid material such as metal having sufficient malleability to be initially bent into appropriate configurations for extending along the medial and lateral sides of the lower leg. The uprights are sufficiently rigid to resist forces in several planes. The uprights resist bending in response to forces in the forward or rear directions (from flexion of the ankle joint) during use. Inasmuch as this resistance to bending can be used to control angular flexion of the ankle joint, as described below, the uprights are also referred to herein as medial and lateral ankle control members. The uprights also resist sideways motion (inversion and eversion) during use. Therefore, the uprights control flexion while preventing inversion and eversion. The uprights also resist torque of the ankle joint. The medial and lateral brackets of the ankle joints are also rotatably affixed to upper portions of corresponding medial and lateral rigid side arms 58 and 80 which, in turn, are rigidly affixed to and extend upwardly above the opposite sides of the shell that forms the foot-supporting shoe.

The uprights are of greater thickness in a region above the brackets 52 and 53 which terminates in a beveled shoulder spaced above each bracket. This region of the uprights avoids metal fatigue arising from torquing of the uprights during use, by spreading the loading as opposed to allowing such loading to be concentrated at one locus on each upright.

Figures 4, 5:
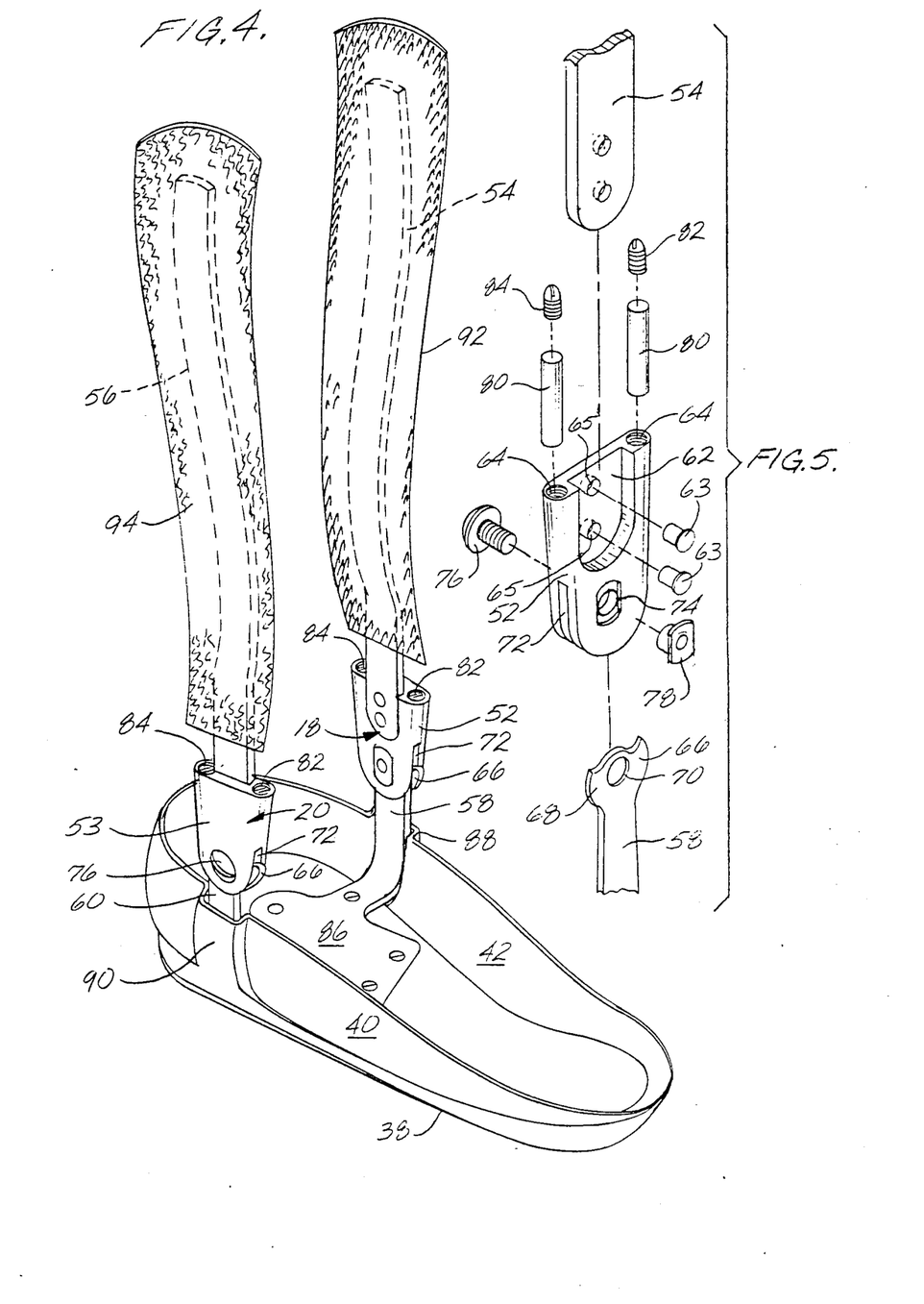
FIG. 4 is a perspective view illustrating a means of attaching the adjustable double action ankle joints to the walker.
FIG. 5 is an exploded perspective view illustrating components of an adjustable double action ankle joint.

Detailed construction of each double action ankle joint is best understood by referring to FIG. 5 which illustrates an exploded view of the medial double action ankle joint 18. The lateral ankle joint 20 is identical in its assembly. The bracket 52 comprises a rigid metal piece having an upwardly opening U-shaped recess 62 in one face of the bracket, and a pair of tapped holes 64 extending along opposite sides of the recess 82. The upper end of the medial side arm 58 is shaped as shown in FIG. 5 and includes front and rear projections 66 and 68 on opposite sides of a pivot axis through a hole 70 in the top of the side arm. The projections serve as front and rear stops to control rotation of the medial upright 54 about a pivot axis through the ankle joint. The upper portion of the side arm 58 fits into a slotted opening 72 in the lower portion of the bracket so the axis of the hole 70 is aligned with an axis through a threaded passage 74 in the lower portion of the bracket. A bearing screw 76 is threaded into a bearing type receptacle 78 fitted in the passage 74 and extending through the hole 70 in the medial side arm 58 to pivotally connect the upper portion of the side arm to the lower portion of the bracket. The slotted opening 72 is oversized with respect to the projecting stop portions 66 and 68 of the side arm so that the bracket and its attached upright can pivot about the axis through the bearing screw 76.

Angular rotation of the bracket relative to the side arm is controlled by a pair of elongated cylindrical metal pins 80 which fit into the lower portions of the tapped holes 64, together with a pair of adjustment screws 82 and 84 threaded into upper portions of the tapped holes 64 for contact with the pins 80. As each screw 82 or 84 is loosened, the amount of angular rotation of the bracket about the axis of rotation can be increased, whereas tightening of the screws 82 and 84 reduces the amount of angular rotation in either the clockwise or counterclockwise directions about the axis through the bracket. Thus, by tightening the front adjustment screw 82 against the pin 80, rotation of the front stop projection 66 of the side arm relative to the bottom of the pin is reduced which, in turn, reduces the forward angular rotation of the bracket about the axis through the bearing screw 76. Similarly, by loosening the rear adjustment screw 84, for example, the amount of angular travel between the rear stop projection 68 of the side arm and the bottom of the pin 80 is increased which, in turn, increases the amount of angular travel of the bracket relative to the side arm toward the rear in FIG. 1. Other adjustments of the double action angle joints are described in more detail below.

Various techniques can be used for securing the rigid side arms 58 and 60 to the foot-supporting shoe. FIG. 4 illustrates a preferred embodiment in which the side arms are integral parts of a U-shaped stirrup having a flat base 86 rigidly affixed to the base of the foot-supporting shoe. Although the base of the stirrup is shown rigidly affixed to the shoe by fasteners, the base of the stirrup also can be molded into the hard plastic shell that forms the shoe, for holding the side arms of the stirrup in a fixed position adjacent the shoe. The upright side arms 58 and 60 project into corresponding outwardly projecting grooves 88 and 90 in the side walls of the shoe. The inside faces of the side arms are thus flush with the inside walls of the shoe.

The medial and lateral uprights 54 and 56 are secured to the leg support by fastening the uprights to the outer face of the flexible padded upper portion 22 of the leg supporting sleeve. The uprights are preferably fastened to the leg support by first inserting them into corresponding Velcro closures 82 and 94 for frictional attachment to the outer faces of the padded upper portion of the sleeve. Each Velcro closure comprises an inner face of a hook type Velcro material and an outer face of a cooperating Velcro pile type material. The Velcro hook type material on the closures frictionally fastens to the Velcro-sensitive outer face of the padded upper portion of the leg supporting sleeve so that the uprights 54 and 56 extend along the medial and lateral sides of the patient's lower leg when the walker is worn. As mentioned above, the uprights are flat bars having extreme rigidity in the forward and reverse directions with respect to the position in which the walker is worn (i.e., in the clockwise or counter-clockwise directions of rotation of the uprights about the axis through the ankle joint). Inasmuch as the brackets 52 and 53 of the ankle joints are rigidly affixed to the corresponding uprights, the uprights and the leg brackets rotate in unison about the transverse axis through the ankle joint. Thus, any angular rotation of the uprights and the brackets relative to the side arms 58 and 80 on the foot-supporting shoe allows a pre-set controlled angular movement of the patient's ankle joint, through the ability of the patient's lower leg to flex relative to the foot about the patient's ankle joint.

The walker is arranged to provide a firm and stable amount of support around the patient's foot and lower leg, preferably with a controlled amount of compression around the lower leg. The foot-supporting shoe includes a pair of front and rear flexible straps 88 and 98, respectively, attached to one side wall of the shoe and arranged to extend over the top of the patient's foot for engagement with D-rings 100 and 102 attached to the other side wall of the shoe. The front and rear straps preferably have front sections of a Velcro pile material and end portions of a Velcro hook type material so that the straps can be threaded through the D-rings, tensioned to the appropriate amount, and then folded back on top of themselves so that the Velcro hook type material can be frictionally attached to the Velcro pile material facing upwardly on the strap to hold the set amount of tension.

Compression for the leg-supporting sleeve is preferably provided by upper, intermediate and lower flexible straps 104, 106 and 108, respectively. The flexible upper strap 104 is illustrated only in FIG. 4 for simplicity, inasmuch as all three straps are identical. Each strap includes an elongated length of a flexible material capable of holding lengthwise tension. The preferred material is nylon. The outer face of each strap has a long section of a Velcro pile material 110, and the outer face of each strap near its free end has a short length of a Velcro hook type material 112. Wear the opposite end of the strap a short section of a Velcro hook type material 114 is secured to the inside face of the strap. A D-ring type fastener 116 is secured to the opposite end of the strap. Each strap is then used by attaching the strap at the desired location on the leg-supporting portion of the walker so that the Velcro hook type section 114 is frictionally attached to the Velcro pile type outer face 94 of the closure for the adjoining upright, as shown in FIG. 3. This firmly affixes the strap to the flexible leg supporting sleeve, after which the strap is wrapped around the circumference of the patient's leg and the free end of the strap is then threaded through the D-ring at the fixed opposite end of the strap. The strap is then tensioned and folded back on itself and wrapped again around the lower leg support to a point where the Velcro type hook material 112 can be fastened to the section 110 of Velcro pile material to hold the compression setting of the strap. All three of the upper, intermediate and lower straps are secured around the lower leg support to apply compression to the lower leg in a similar manner. Preferably, as shown in FIG. 2, the locations of the D-rings can be alternated between opposite sides of the front closure of the lower leg support.

Figure 6:
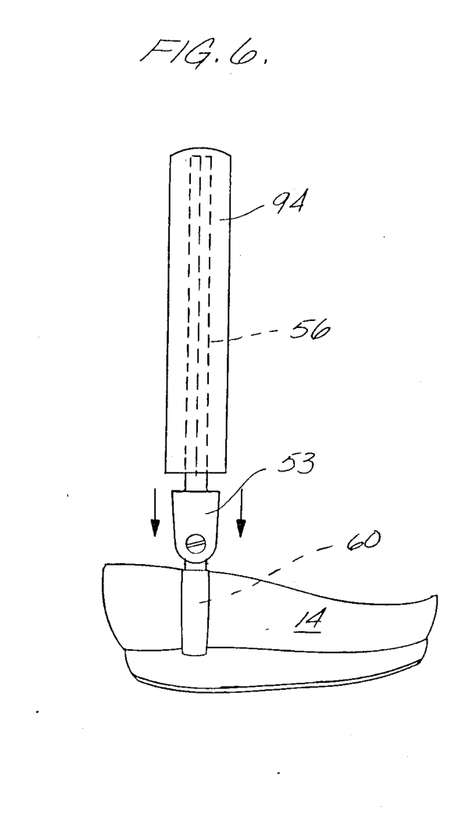
FIG. 6 is a schematic view illustrating a neutral setting of the ankle joint.

In use, the walker is applied to the patient's foot and lower leg by first opening the flexible padded sleeve along its entire length and placing the patient's foot on the inside portion of the padding that overlies the foot supporting shoe. The padding is closed snugly around the patient's foot and the upper portion of the flexible padding is closed snugly around the patient's lower leg. This naturally provides a continuous flexible padding wrapped not only around the lower leg and the foot but also around the patient's ankle region. The flexible straps 96 and 98 are fastened over the patient's foot to firmly secure the patient's foot inside the rocker. The flexible straps 104, 106 and 108 also are firmly wrapped circumferentially around the patient's lower leg to apply compression to the lower leg to hold the walker firmly in place providing continuous support along the lower leg through the ankle region to the patient's foot. The lateral and medial double action ankle joints are then set to control the ankle motion of the walker, depending upon the type of rehabilitation therapy the walker is intended to promote. FIG. 6 illustrates a neutral setting of the walker which is normally used in an early stage of the rehabilitation process when the medial and lateral uprights 54 and 56 are held in a fixed angular position relative to the rocker so that no angular motion is produced during walking. To produce the neutral setting, the front and rear screws 82 and 84 are each turned equally until the uprights are held in a fixed perpendicular position relative to the floor. By turning the screws the pins 80 are forced down into engagement with the front and rear stops 66 and 68 on the side arms 58 and 60 to prevent relative rotation between the brackets 52 and 53 and the side arms of the rocker.

Figure 7:
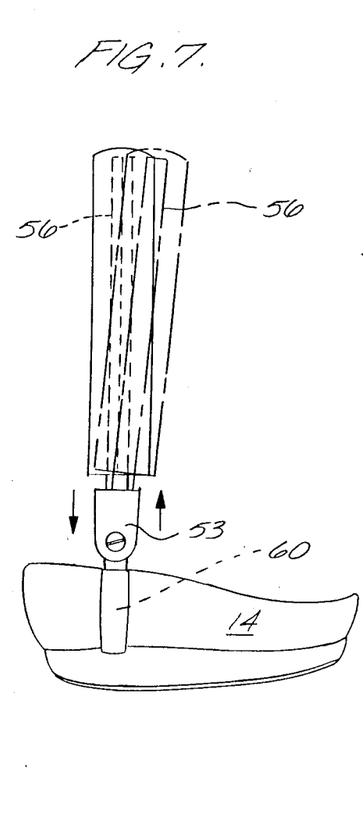
FIG. 7 is a schematic view illustrating a dorsiflexion setting of the ankle joint.
Figure 8:
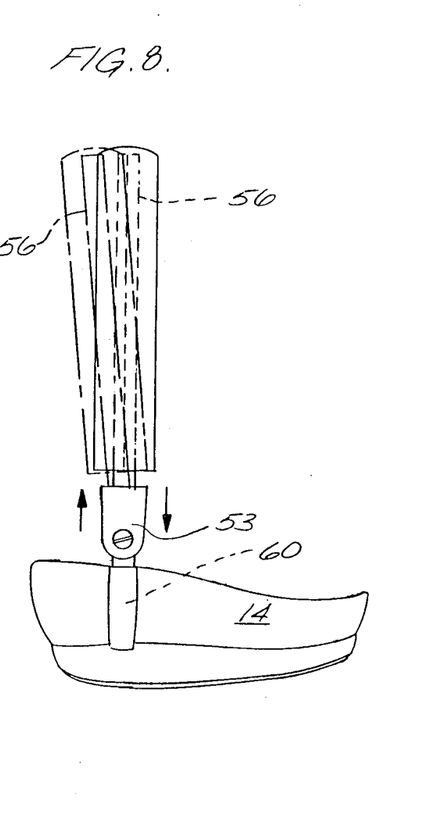
FIG. 8 is a schematic view illustrating a plantar flexion setting of the ankle joint.

FIGS. 7 through 10 illustrate various means of adjusting the range of motion settings for the walker. In one embodiment the adjustment screws and their corresponding pins are arranged relative to the projecting shoulders on the side arms of the rocker so that one revolution of either adjustment screw will produce a 5° angular rotation between the uprights and the floor. FIG. 7 illustrates the setting of the walker for a dorsiflexion angle in which the front screw is loosened and the rear screw is tightened (to force the rear pin against the stop 68) until rotation through a dorsiflexion angle only is obtained. The uprights cannot rotate from neutral into a plantar flexion angle. FIG. 8 shows the adjustment to set a plantar flexion angle where the rear adjustment screw is loosened and the front screw is tightened against the front stop 66 until the desired amount of plantar flexion has been set. In this arrangement the uprights do not rotate past neutral into a dorsiflexion angle.

Figures 9, 10:
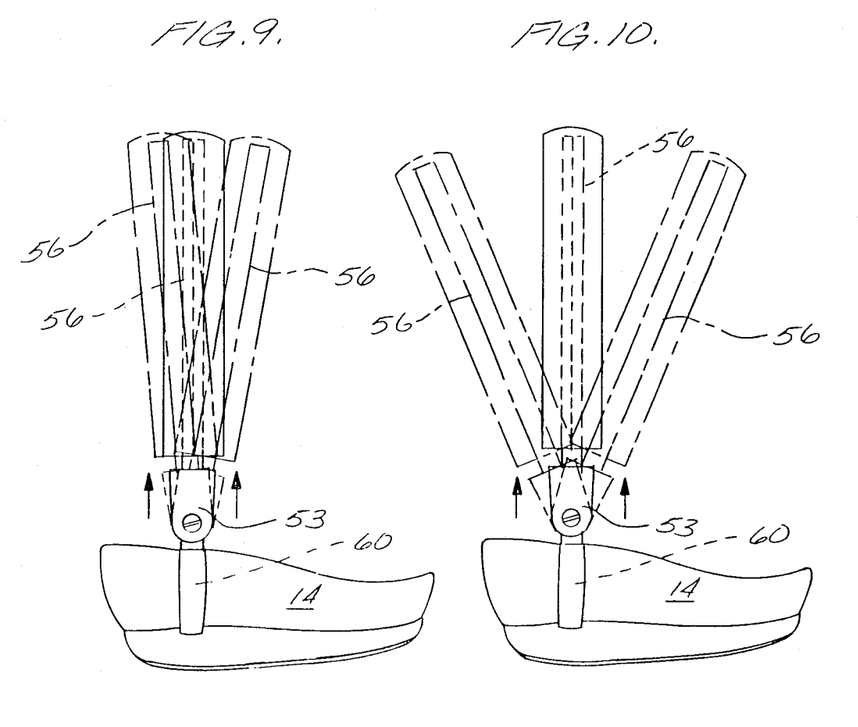
FIG. 9 is a schematic view illustrating an ankle joint setting for limited dorsiflexion and plantar flexion.
FIG. 10 is a schematic view illustrating a setting of the ankle joint for maximum dorsiflexion and plantar flexion.

FIG. 9 shows an arrangement for providing limited motion in dorsiflexion and plantar flexion. In this arrangement the dorsiflexion angle is greater than the plantar flexion angle. For instance, the front adjustment screws can be loosened two full turns to set a 10° dorsiflexion angle, while both rear screws are loosened one full turn to set 5° of travel in plantar flexion.

FIG. 10 illustrates the adjustment for unlimited motion of 22½° dorsiflexion and 22½° plantar flexion where both front and rear screws are loosened fully. This allows a total range of 45° of ankle motion.

As shown best in FIG. 1, a gauge 118 on the lateral and medial side arms, below each bracket, provides a means for accurately setting the desired range of motion.

Thus, a patient wearing the walker during rehabilitation can rotate the ankle joint through a controlled angle during weight-bearing, while the physician controls the specific range of angular motion of the ankle joint depending upon the type of injury. This combination of angular motion plus weight-bearing for a given injury quickens the healing process. Once the ankle joint begins to heal following an ankle fracture or a severe ankle sprain, movement of the ankle joint alone can assist in more rapid healing. Walking with weight on the injured joint also assists in speeding the healing process. With the walker of this invention, the physician allows the patient to apply weight to the injured joint and, in combination, permits a certain angle of flexion of the ankle joint depending upon the extent of pain-free angular motion the injury will sustain. The physician can also set the specific range of motion depending upon the type of injury to the ankle joint. For instance, an injury to the Achilles' tendon may be treated by allowing the patient to walk in plantar flexion only with weight-bearing until the tendon heals. Other ligament tears can be treated by ankle motion in dorsiflexion only until healing is more complete, followed by a greater angular motion in combined dorsiflexion and plantar flexion. In addition, the walker provides static support for the traumatized joint and minimizes edema. The walker protects the joint from stress during weight bearing and still allows motions of plantar flexion and dorsiflexion. The walker thus provides stability, support and controlled compression and gives continuous and optimum walking assistance during combined flexion and weight bearing.

What is claimed is:

1. A controlled motion ankle fracture walker, comprising:
    a rigid foot-supporting shoe having means for releasable attachment to the foot of a patient, the shoe extending under the patient's foot and along lateral and medial sides of the foot below the ankle joint of the patient, the foot-supporting shoe having a curved bottom for rolling contact with the ground to provide a rocking heel-to-toe motion of the foot of the Patient, the shoe having rigid lateral and medial side arms rigidly affixed to and extending from corresponding sides of the shoe to the vicinity of the lateral and medial sides of the ankle joint of the patient,
    leg support means for releasable attachment to the leg of the patient above the ankle joint of the patient, the leg support means having rigid lateral and medial ankle rotation control members for extending along the lateral and medial sides of the patient's leg above the ankle joint, and means for rigidly affixing the lateral and medial ankle rotation control members to the leg support means to hold the control members in a fixed position on the lateral and medial sides of the patient's lower leg above the ankle joint, and
    adjustable double action ankle joints adjacent the lateral and medial sides of the ankle joint, comprising lateral pivot means rotatably interconnecting the lateral ankle rotation control member to the lateral side arm of the foot-supporting shoe and medial pivot means rotatably interconnecting the medial ankle rotation control member to the medial side arm of the foot-supporting shoe so that the control members are rotatable through an angle relative to the corresponding side arms of the shoe, said rotation being about a transverse pivot axis through the ankle joint of the patient, said angle defining an arc of ankle rotation passing from a first angular position in dorsiflexion through a neutral upright position to a second angular position in plantar flexion the double action ankle joints further including angle adjustment means for selectively setting an angle at which the control members are held relative to the side arms of the shoe or for selectively controlling an arc through which the control members rotate about the pivot means, so that the control members can be selectively set in a fixed position at a preset dorsiflexion angle, a neutral position, or at a pre-set plantar flexion angle; or the control members selectively allowed to rotate continuously through a controlled angular range of motion within pre-set limits in dorsiflexion only, in plantar flexion only, or in combined dorsiflexion and plantar flexion,
    the leg support means being interconnected to the foot-supporting shoe so that the ankle joint of the patient has freedom to flex about said pivot axis under the control of said double action ankle joints for permitting angular rotation of the leg support means relative to the shoe about the pivot axis through the ankle joint of the patient so that a patient wearing the walker can apply weight to the ankle joint as the shoe rocks the foot through a heel-to-toe walking gait while the double action ankle joints control the pre-set angle or the range of angular motion of the patient's ankle joint within said pre-set limits.

2. Apparatus according to claim 1 in which the angle adjustment means include first adjustment means for adjustably setting the maximum limit of angular travel of the leg position control members in a forward direction, and second adjustment means for adjustably setting the maximum limit of angular travel of the leg position control member in the rear direction.

3. Apparatus according to claim 1 in which either of the ankle control members or their corresponding side arms has first and second rigid stops spaced to the front and rear of the pivot axis; and the angle adjustment means comprise separate rigid adjustment means movable toward or away from the rigid stops and setable in a fixed position to adjust the amount of angular travel between each stop and the corresponding adjustment means for controlling the amount of angular travel of the control members in dorsiflexion and plantar flexion, respectively.

4. Apparatus according to claim 3 in which the first stop means controls the angular position from neutral to a dorsiflexion angle and a second stop means controls the angular position from neutral to a plantar flexion angle.

5. Apparatus according to claim 1 including an elongated generally L-shaped sleeve of a flexible material wrapped around a lower leg and extending continuously past the ankle joint and along at least a portion of the foot, and in which the leg support means is releasably secured around the sleeve and the foot supporting shoe also is secured to the foot around the sleeve.

6. Apparatus according to claim 1 in which the side arms are rigid uprights on a U-shaped bracket having at least its transverse bottom member rigidly affixed to the base of the shoe.

7. Apparatus according to claim 1 including an angular gauge on the adjustable double action ankle joints for indicating the number of degrees of rotation of the control members through each arc in dorsiflexion and plantar flexion.

8. Apparatus according to claim 1 in which the leg support includes means for applying compression around the leg above the ankle joint.

* * * * *

UNITED STATES PATENT AND TRADEMARK OFFICE
CERTIFICATE OF CORRECTION

PATENT NO. : 4,771,768
DATED : September 20, 1988
INVENTOR(S) : George E. Crispin It is certified that error appears in the above-identified patent and that said Letters Patent is hereby corrected as shown below:

In the Abstract:

Line 10, change "pivotly" to -- pivotally --.

In the Specification:

Column 2, line 5, change "propriception" to -- proprioception --.
Column 2, line 20, change "weightbearing" to -- weight-bearing --.
Column 2, line 31, change "fot" to -- for --.
Column 3, line 18, change "weightbearing" to -- weight-bearing --.
Column 3, line 58, change "18" to -- 16 --.
Column 4, line 19, change "28" to -- 26 --.
Column 4, line 22, change "ofthe" to -- of the --.
Column 4, line 49, change "footsupporting" to -- foot-supporting --.
Column 4, lines 56 and 57, after "foot-supporting" delete "supporting"
Column 4, line 61, change "spacedapart" to -- spaced apart --.
Column 4, line 68, change "footsupporting" to -- foot-supporting --.
Column 5, line 32, change "80" to -- 60 --.
Column 5, line 34, change "forms" to -- form --.
Column 5, line 50, change "82" to -- 62 --.
Column 6, line 23, change "angle" to -- ankle --.
Column 6, line 64, change "80" to -- 60 --.
Column 6, line 65, change "pre-set" to -- preset --.
Column 7, line 5, change "88" to -- 96 --.

UNITED STATES PATENT AND TRADEMARK OFFICE
CERTIFICATE OF CORRECTION

PATENT NO. : 4,771,768
DATED : September 20, 1988
INVENTOR(S) : George E. Crispin It is certified that error appears in the above-identified patent and that said Letters Patent is hereby corrected as shown below:

Column 7, line 28, change "Wear" to -- Near --.
Column 7, line 32, change "Fach" to -- Each --.

In the Claims:

Column 9, line 26, change "Patient" to -- patient --.
Column 10, lines 2 and 5, change "pre-set" to -- preset --
    (both occurrences).
Column 10, lines 18 and 19, change "pre-set" to -- preset--
    (both occurrences).

Signed and Sealed this

Fourteenth Day of March, 1989

Attest:

*Attesting Officer*

DONALD J. QUIGG

*Commissioner of Patents and Trademarks*